United States Patent [19]

Patel

[11] Patent Number: 5,167,657

[45] Date of Patent: Dec. 1, 1992

[54] PLASTIC COMPOSITION WITH ANTI-HEMOLYTIC EFFECT

[75] Inventor: Indrajit Patel, Algonquin, Ill.

[73] Assignee: Baxter International Inc., Deerfield, Ill.

[21] Appl. No.: 837,581

[22] Filed: Feb. 18, 1992

Related U.S. Application Data

[60] Continuation of Ser. No. 674,530, Mar. 22, 1991, abandoned, which is a division of Ser. No. 494,045, Mar. 15, 1990, Pat. No. 5,100,401, which is a division of Ser. No. 270,006, Nov. 14, 1988, Pat. No. 5,026,347.

[51] Int. Cl.$^5$ .................... A61B 19/00; C08K 5/10; A01N 1/02
[52] U.S. Cl. .................... 604/410; 524/310; 524/311; 435/2
[58] Field of Search ............ 604/410, 403, 408, 409; 623/11; 524/110, 114, 291, 310, 311, 377; 521/84.1; 560/180; 435/2

[56] References Cited

U.S. PATENT DOCUMENTS

| | | |
|---|---|---|
| 2,325,983 | 8/1943 | Sarbach . |
| 2,633,456 | 3/1953 | Vaughan . |
| 2,766,273 | 10/1956 | Bruins et al. . |
| 2,956,855 | 10/1960 | Havens . |
| 3,231,529 | 1/1966 | Kuhn et al. . |
| 3,239,555 | 3/1966 | Miksch et al. . |
| 3,284,389 | 11/1966 | Kane . |
| 3,370,032 | 2/1968 | Potter . |
| 3,396,121 | 8/1968 | Miksch et al. . |
| 3,459,736 | 8/1969 | Dalibor . |
| 3,479,308 | 11/1969 | Gattenby et al. . |
| 3,557,030 | 1/1971 | Simons . |
| 3,818,071 | 6/1974 | Chilton . |
| 3,822,232 | 7/1974 | Huang et al. . |
| 3,879,346 | 4/1975 | Friedrich et al. . |

(List continued on next page.)

FOREIGN PATENT DOCUMENTS

| | | |
|---|---|---|
| 0138147 | 10/1983 | European Pat. Off. . |
| 88/9007985 | 1/1988 | European Pat. Off. . |
| 1200528 | 12/1960 | Fed. Rep. of Germany . |
| 218105A1 | 10/1983 | Fed. Rep. of Germany . |
| 53-29352 | 9/1976 | Japan . |
| 57-207635 | 6/1981 | Japan . |
| 2065446B | 7/1981 | United Kingdom . |

OTHER PUBLICATIONS

*Fundamentals of Organic Chemistry*, ©1982, John Wiley & Sons, pp. 154-155.
Shettino and La Rotonda, *Sulla Cessione De Additivi Da Parte Di Presidi Chirurgici Contenitori In PVC Per USO Farmaceutico. Di Evidenziazione Cromatografica Di Plastificanti A Base Di Citrati E. Ftalati Alchilci*, Sezione de Napoli—Seduto del 29 luglio 1969.
Hollingsworth, *Pharmacological Properties of the Plasticizer Acetyl-n-tributyl Citrate, and its Extraction from Poly (vinyl chloride) Tubing*, J. Biomed. Mater. Res., vol. 9, pp. 687-697 (1975).
Snyder et al., *Stability of Red Cell Antigens and Plasma Coagulation Factors Stored in New Formulation Plastic Blood Containers*, Transfusion (1983).
Hull et al., *Citric Acid Esters as Plasticizers for Medical--Grade PVC*, Modern Plastics (1984).
Pfizer Chemicals Data Sheets: BA, BB, BC, published Jan. 1982, Apr. 1982 and Oct. 1982.

*Primary Examiner*—C. Fred Rosenbaum
*Assistant Examiner*—Ronald Stright, Jr.
*Attorney, Agent, or Firm*—Andrew G. Kolomayets; Gary W. McFarron; Bradford R. L. Price

[57] ABSTRACT

A plastic composition is disclosed which has particular application in the manufacture of blood bags and other medical products. The composition has anti-hemolytic effects when used in the storage of red blood cells. In connection with one aspect of the present invention, the plastic composition comprises the combination of a non-PVC plastic and a selected quantity citrate ester sufficient to suppress hemolysis of red blood cells. The non-PVC material is preferably a polyolefin copolymer. Materials other than citrate ester may also be used with polyolefin as a hemolysis suppressant.

28 Claims, 2 Drawing Sheets

U.S. PATENT DOCUMENTS

| | | |
|---|---|---|
| 3,932,656 | 1/1976 | Ramwell et al. ........................ 424/16 |
| 3,936,403 | 2/1976 | Sakaguchi et al. . |
| 4,061,844 | 12/1977 | Itoh et al. . |
| 4,140,162 | 2/1979 | Gajewski et al. . |
| 4,207,224 | 6/1980 | Randell et al. . |
| 4,222,379 | 9/1980 | Smith . |
| 4,286,597 | 9/1981 | Gajewski et al. . |
| 4,300,559 | 11/1981 | Gajewski et al. . |
| 4,301,800 | 11/1981 | Collins . |
| 4,326,025 | 4/1982 | Buckles et al. . |
| 4,328,319 | 5/1982 | Osipow et al. ........................ 521/78 |
| 4,336,148 | 6/1982 | Wirth et al. . |
| 4,375,509 | 3/1983 | Buckles et al. . |
| 4,451,259 | 5/1984 | Geissler et al. . |
| 4,505,708 | 3/9185 | Gajewski et al. . |
| 4,507,123 | 3/1985 | Yoshida . |
| 4,507,387 | 3/1985 | Gajewski et al. . |
| 4,588,583 | 5/1986 | Pietsch et al. . |
| 4,710,532 | 12/1987 | Hull et al. . |
| 4,711,922 | 12/1987 | Hull et al. . |
| 4,789,700 | 12/1988 | Hull et al. . |
| 4,824,893 | 4/1989 | Hull et al. . |
| 4,837,046 | 6/1989 | Sato et al. ............................ 424/41 |
| 4,870,204 | 9/1989 | Hull et al. . |
| 4,883,905 | 11/1989 | Hull et al. . |
| 4,892,967 | 1/1990 | Hull et al. . |
| 4,931,583 | 6/1990 | Hull et al. . |
| 4,954,649 | 9/1990 | Hull et al. . |

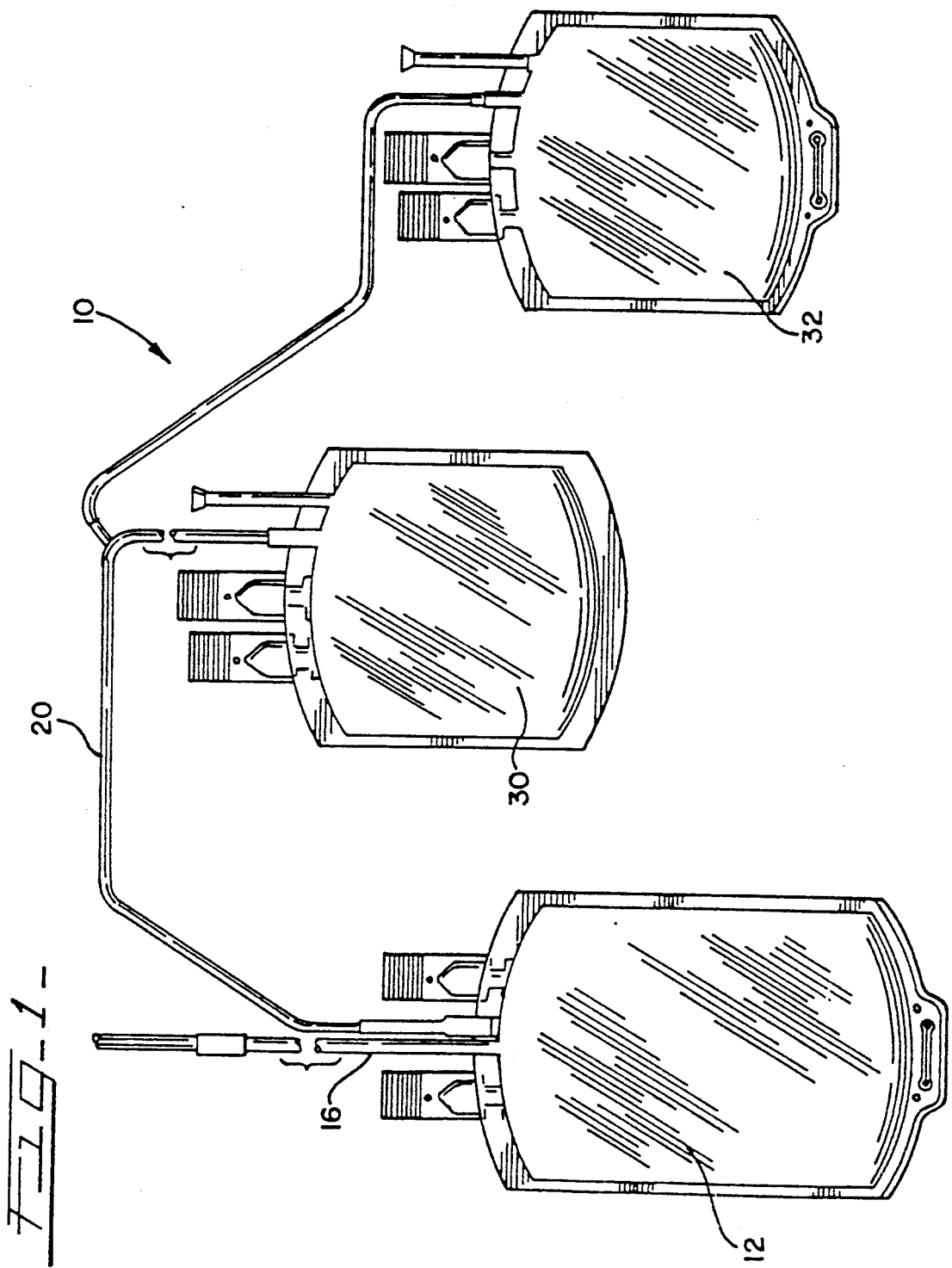

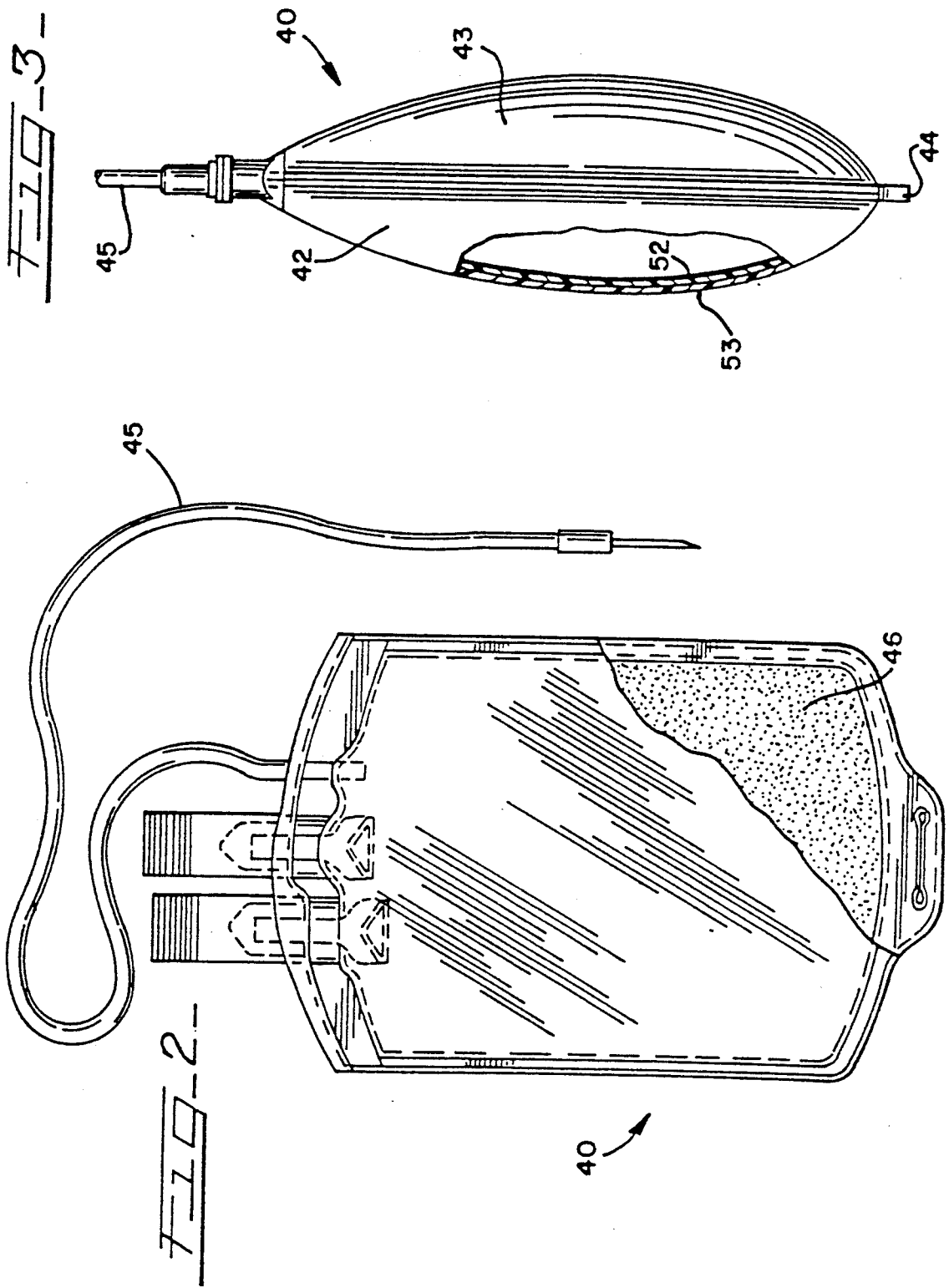

PLASTIC COMPOSITION WITH ANTI-HEMOLYTIC EFFECT

This is a continuation of copending application(s) Ser. No. 07/674,530 filed on Mar. 22, 1991, now abandoned which is a division of U.S. application Ser. No. 494,045 filed Mar. 15, 1990, now U.S. Pat. No. 5,100,401 which is a division of U.S. application Ser. No. 270,006 filed Nov. 14, 1988, now U.S. Pat. No. 5,026,347.

BACKGROUND OF THE INVENTION

The present invention relates generally to a flexible, plastic composition and to the method for making and using such a plastic composition and containers thereof, wherein the plastic is capable of suppressing the hemolysis of red blood cells stored in containers made of the plastic composition.

Currently, the most widely used material for blood and blood component containers is polyvinyl chloride (PVC), with a sufficient amount of plasticizer added to soften the otherwise brittle PVC. Plasticizers from the group of phthalate esters, and, in particular, di-2-ethylhexylphthalate (DEHP), have often been used in combination with the PVC resins. Although the use of DEHP plasticizer with plastic blood bags has generally worked satisfactorily, it is not without certain drawbacks.

As mentioned above, the rigid nature of PVC requires that it be softened with a plasticizer. However, it has been found that a small amount of plasticizer will leach into red blood cells stored within plasticized bags. Although no adverse physiological effects have been detected in patients receiving blood from DEHP plasticized containers, it is nonetheless desirable to minimize exposure of the patient to compounds not normally found in the body such as DEHP.

On the other hand, it is known in the prior art that the presence of DEHP has a beneficial effect on red blood cells stored within containers plasticized with DEHP. Specifically, red blood cells stored within containers plasticized with DEHP and perhaps other plasticizers such as triethylhexyltrimellitate (TEHTM) exhibit a much lower level of hemolysis than red blood cells stored in plasticizer-free containers.

These known effects of DEHP have been utilized in the manufacture of multiple bag systems currently employed in blood storage and processing. Multi-bag systems usually include two or more bags wherein, through centrifuging and separation, each bag ultimately contains a different blood component, for example, red blood cells, blood platelets, and plasma. Since hemolysis is a measure of the destruction of red blood cells, it has been recognized that the red blood cell container may include a plasticizer to reduce hemolysis, while at the same time, the bags containing the other blood components, such as plasma or platelets, ought to be plasticizer free to reduce unnecessary exposure to DEHP. While such multi-bag systems have definite advantages, the need for containers made of different materials requires heightened quality control efforts and results in more expensive manufacturing costs.

As a result, the prior art discloses several efforts to develop plastic materials or bag constructions suitable for storing blood (and the various blood components) and exhibiting the antihemolytic effect of DEHP-plasticized polyvinyl chloride. See, e.g., U.S. Pat. No. 4,300,599.

One such effort described in U.S. Pat. No. 4,301,800 is to combine a plasticizer-free outer bag with a plasticized insert. Other prior art includes U.S. Pat. No. 4,507,387 which describes a combination of plasticizers, one of which, DEHP, leaches and the other of which did not leach. Additionally, U.S. Pat. No. 4,140,162 describes a plasticizer-free polyolefin, which is said to be a suitable, flexible, autoclavable, chlorine-free material with excellent gas ($O_2$ and $CO_2$) permeability characteristics for storing blood and the various blood components, although in the absence of plasticizer, hemolysis of the red blood cells remains relatively higher than preferred.

The prior art has also described further plasticizers said to be compatible with PVC used in blood transfer and storage bags. U.S. Pat. Nos. 4,710,532 and 4,711,922, for example, suggest that citrate esters used as plasticizers for PVC are more easily metabolized by the body than DEHP.

Despite these efforts, the prior art has not been able to provide a flexible, chlorine-free composition suitable for use as a blood bag and capable of suppressing hemolysis of red blood cells stored within the bag, without the drawbacks associated with DEHP.

Accordingly, a general object of the present invention is to provide a plastic composition which does not suffer from the drawbacks described above.

SUMMARY OF THE INVENTION

The present invention is generally directed to a flexible, plastic composition capable of suppressing the hemolysis of red blood cells, containers employing such compositions and the method of making and using such containers to suppress the hemolysis of red blood cells.

As employed in the manufacture and use of blood bags, the flexible, autoclavable, plastic composition comprises a non-PVC plastic and a material selected from the group consisting of either triethylhexyltrimellitate (TEHTM) and citrate ester. The plastic composition may further include polypropylene.

In the preferred embodiment, the non-PVC plastic is comprised of a polyolefin copolymer containing a central block of ethylene and butylene units with terminal blocks of polystyrene. A suitable polyolefin copolymer is described in U.S. Pat. No. 4,140,162, incorporated by reference herein. With a polyolefin copolymer, di-2-ethylhexylphthalate may also be used as a hemolysis suppressant.

Also in accordance with the preferred embodiment, the invention contemplates a citrate ester of the formula:

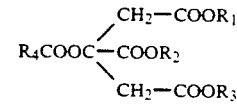

where:
$R_1$, $R_2$, and $R_3 = CH_3$ to $C_{18}H_{37}$
$R_4 = CH_3$ to $C_7H_{15}$ More specifically, the citrate ester may be either acetyltri-n-hexyl citrate, acetyltri-n(hexyl/octyl/decyl) citrate, acetyltri-n-(octyl/decyl) citrate, or most preferably, n-butyryltri-n-hexyl citrate. These citrate esters provide a controlled leaching of the citrate ester into the blood in order to suppress the hemolysis of red blood cells. In the preferred embodiment, the plastic composition includes between 55% to 65% by weight of the polyolefin copolymer, 15% to 25% by weight of citrate ester, and 20% to 30% by weight of polypropylene.

The plastic composition of the present invention may be used to define at least a portion of the interior surface of a plastic container. Alternatively, the container walls may be made solely of the plastic composition described above. Where the bag consists of a plurality of layers, at least a portion of the innermost layer may be of the plastic composition while the outer layer(s) may be made of a different material or the plastic composition may be applied as an emulsion to the bag.

The containers described above may be used independently or as part of a multiple container system wherein at least one but preferably all of the containers are made of the plastic composition of the present invention.

Another object of the present invention is to provide a method of making a flexible, plastic container for storing red blood cells and capable of suppressing the hemolysis of the red blood cells. This method includes providing a non-PVC plastic of the type described above and mixing the copolymer with either triethylhexyltrimellitate or, preferably citrate ester. The resultant material is then extruded into a film and formed into a container. In the preferred embodiment, the non-PVC plastic is a polyolefin copolymer. Also, in the preferred embodiment, the method includes adding another polyolefin such as polypropylene.

Finally, the present invention also provides a method for suppressing the hemolysis of red blood cells. This method includes providing a flexible, autoclavable plastic container having at least a portion of the interior surface thereof formed of a plastic composition comprised of a non-PVC plastic and a second material selected from the group of triethylhexyltrimellitate and citrate ester, wherein the quantity of the second material is capable of suppressing the hemolysis of red blood cells within the container. The method further includes introducing a quantity of red blood cells into the container and maintaining the quantity of red blood cells within the container for a selected period of time.

Further features of the present invention will become more fully apparent in the following description of the embodiments and from the appended claims.

DESCRIPTION OF DRAWINGS

FIG. 1 is a plan view of a multi-bag system.

FIG. 2 is a plan view of blood bag 40 made in accordance with the present invention, with a portion broken away to depict an alternative embodiment of the present invention.

FIG. 3 is a side view of a blood bag with a portion broken away depicting an alternative embodiment of the present invention.

Referring now to FIG. 1, blood bag system 10 includes generally a donor bag 12, transfer tubing 20, and two transfer bags 30 and 32.

Donor bag 12 is made of the flexible, autoclavable plastic composition of the present invention, capable of suppressing hemolysis of red blood cells stored within the donor bag 12. Generally, blood is collected through the donor tube 16 into donor bag 12, wherein the blood is mixed with a blood preservative. During storage, the presence of plasticizer in the plastic composition comprising the container wall of the donor bag suppresses the rate of red blood cell hemolysis. In normal applications, the collected blood is centrifuged, with the red cells settling to the bottom of the donor bag 12, and the platelet-rich plasma and other components being expressed through the transfer tubing 20 into transfer bag 30 where it is also centrifuged. The platelet rich plasma settles to the bottom of transfer bag 30, while the platelet poor plasma is expressed to transfer bag 32. Donor bag 12 containing the red blood cells is then separated from the multi-beg system 10 and sealed.

Transfer bags 30 and 32 may also be comprised of the plastic composition of the present invention or alternatively be comprised of a plasticizer-free polyolefin or other material with other additives which exhibit the improved gas transmission characteristics for platelet storage similar to the plastic composition of the present invention.

Blood bag 40, depicted in FIG. 3, shows the container walls comprised of plastic sheets 42 and 43 sealed together at the periphery 44 in a well known manner and containing a blood collection tube 45. Blood bag 40 may be utilized as either a donor bag or a transfer bag as described above. In one embodiment of the present invention, both plastic sheets 42 and 43 forming the bag walls may be comprised entirely of the plastic composition of the present invention. FIG. 3 also shows an alternative embodiment of the present invention. In this embodiment, blood bag 40 is comprised of at least two layers wherein the innermost layer 52 comprises the plastic composition of the present invention, while the outer layer 53 is made of a different material which may be co-extruded with the plastic composition of the present invention. Alternatively, the outer portion of the container wall may be comprised of a first material whereas the innermost layer of the bag 45 is comprised of the plastic composition of the present invention, applied in the form of an emulsified layer as depicted in FIG. 2.

Finally, transfer tubing 20 and donor tube 16 may also be of the plastic composition of the present invention.

PLASTIC

The plastic composition of the present invention comprises a non-PVC plastic or other chlorine-free plastic suitable for use as a blood bag. In the preferred embodiment, the non-PVC plastic is a polyolefin copolymer.

Generally, the copolymer is comprised of a central block of at least two polyolefins with terminal blocks of polystyrene. In the preferred embodiment, the central block comprises from 50% to 85% by weight of equal proportions of ethylene and butylene units. The polyolefin copolymer is commercially available under the trademark KRATON G from the Shell Chemical Company. The polyolefin copolymer and the characteristics thereof are further described in U.S. Pat. No. 4,149,162 which is incorporated by reference herein.

ESTER

The plastic composition of the present invention preferably comprises between 15% to 25% of a second material such as an ester. Esters such as di-2-ethylhexylphthalate, triethylhexylmellitate (TEHTM) or citrate ester may be combined with the polyolefin copolymer. The preferred citrate esters have the advantage of being more easily metabolized by the body than either DEHP or TEHTM and are preferred.

In the preferred embodiment, the plastic composition includes citrate esters of the formula:

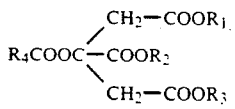

where:

$R_1$, $R_2$, and $R_3 = CH_3$ to $C_{18}H_{37}$
$R_4 = CH_3$ to $C_7H_{15}$

The use of this ester may result in a controlled leaching from the plastic composition in order to suppress hemolysis of red blood cells within a container made of such material. The controlled leaching, for example, may be obtained by varying the quantity of citrate ester or by selecting a particular ester of the desired molecular weight or length of carbon chain. Higher molecular weights and longer carbon chains are believed to result in a lesser amount of leaching. By selecting from these and other variables, the amount of leaching and therefore the resultant hemolysis levels may be controlled.

Specifically, the citrate ester used may be acetyltri-n-hexyl citrate, acetyltri-n-(hexyl/octyl/decyl) citrate, acetyltri-n-(octyl/decyl) citrate and most preferably, n-butyryltri-n-hexyl citrate. Such esters may be commercially available from the Morflex Chemical Company of Greensboro, N.C. The physical and chemical characteristics of the above-mentioned citrate esters are more fully described in U.S. Pat. Nos. 4,710,532 and 4,711,922 which are incorporated by reference herein.

In addition to the polyolefin copolymer and ester, the plastic composition of the present invention may also include polypropylene, i.e., a polyolefin consisting essentially of propylene units. The polypropylene provides stiffness and resistance to heat generally, and to the stress of autoclaving specifically. The plastic composition may comprise from 20% to 30% by weight of polypropylene. The polypropylene may be added to the polyolefin-ester mixture after the ester has been substantially absorbed.

Further additives may include ethyl vinyl acetate and an antioxidant. Basically, the plastic composition comprises a major quantity of the olefin copolymer and a minor amount of an ester. It is preferred to use from about 15% to 25% weight of the ester, which provides the desired suppression of the hemolysis and provides a composition having suitable handling properties. Less than 15% of the ester may be used but the suppression of hemolysis may decrease. More than 25% of the ester may also be used, but the suppression of hemolysis is not significantly improved and the mechanical properties of the plastic are affected.

Generally speaking, the balance of the composition may be polyolefin copolymer. However, it is preferred to use from about 20% to 30% by weight of polypropylene and 55% to 65% of the olefin copolymer in order to produce a plastic composition which has superior mechanical properties, i.e., greater stiffness and durability. More than 30% polypropylene may be used if additional stiffness is desired.

The method of fabricating the plastic composition includes the initial step of slowly mixing (approximately 1000 RPM) between 55% and 65% by weight of the polyolefin copolymer. The copolymer is mixed to a temperature of approximately 140° F. at which point 15% to 25% by weight of ester is added to the copolymer material. The two reactants are mixed until the ester is substantially absorbed.

As employed in the manufacture of blood bags, the plastic composition described above may be further pelletized and extruded into sheets of film of approximately 0.011" to 0.012" in thickness. The film is then formulated into containers by a process known to those skilled in the art. The film is radio frequency (R.F.) or induction sealable and is solvent bondable for the purpose of port and tubing attachment. The plastic composition shows good low temperature and gas ($O_2$ and $CO_2$) permeability characteristics. The bag made of the plastic composition may be sterilized by steam, ethylene oxide or gamma ray.

When used in blood bag manufacture, the plastic composition may comprise the container walls or only portions of the interior surface of the bag. Alternatively, it is possible to co-extrude the plastic composition with a second material wherein the plastic composition of the present invention comprises the innermost layer of a multi-layered bag, while the outer layer(s) of the bag are made of a different plastic material.

The completed and sterilized bag may then be substantially filled with red blood cells and blood preservatives. The bag (with contents) may then be stored for a period of time.

The following examples are for illustrative purposes only, and are not for the purpose of limiting the invention of this application, which is defined in the claims below.

EXAMPLE 1

A plastic composition was prepared from 55% by weight of the KRATON G copolymer, 15% by weight of n-butyryltri-n-hexyl citrate ester and 30% by weight of polypropylene. The plastic composition was mixed for less than fifteen minutes, pelletized and extruded into a film of approximately 0.011" in thickness. The material was then successfully fabricated into transparent, flexible, collapsible bags. The bags were autoclaved, filled with blood, and stored for a period of several weeks. Anticoagulant (known by its trade name of ADSOL and available from BAXTER International of Deerfield, Ill.) consisting of 2.2 g/dl of dextrose monophosphate, 0.027 g/dl of adenine, 0.75 g/dl of mannitol and 0.9 g/dl of NaCl was also added to the bag. Table 1 summarizes the physical properties of the blood stored within bags made by the method described above. Table 2 compares the hemolysis and plasma hemoglobin levels found in a blood bag made in accordance with the method described in this example with a control bag made of PVC with DEHP plasticizer. All values are expressed as means.

TABLE 1

| | Characteristics of blood stored in containers made in accordance with the present invention | | | | |
|---|---|---|---|---|---|
| Days of Storage | $PCO_2$ (mm/hg) | $PO_2$ (mm/hg) | Glucose (mg/dl) | PLHMGB (mg/dl) | Hemol % |
| 0 | 66.30 | 38.00 | 828.50 | 2.25 | 0.01 |
| 7 | 89.10 | 52.50 | 784.00 | 15.80 | 0.04 |
| 14 | 98.80 | 71.00 | 770.00 | 26.90 | 0.07 |
| 21 | 97.05 | 119.00 | 764.00 | 54.00 | 0.15 |
| 28 | 86.55 | 233.00 | 649.00 | 122.00 | 0.33 |
| 35 | 79.25 | 259.51 | 657.00 | 168.00 | 0.45 |
| 42 | 72.30 | 193.50 | 632.00 | 224.50 | 0.60 |

TABLE 2

Comparison of hemolysis and plasma hemoglobin levels of blood stored in containers made in accordance with the present invention (designated as V-4292) and blood stored in conventional DEHP plasticized PVC bags

| Days of Storage | Hemolysis % | | Plasma Hemoglobin (mg/dl) | |
|---|---|---|---|---|
| | V-4292 | PVC | V-4292 | PVC |
| 0 | 0.01 | 0.01 | 2.25 | 4.47 |
| 7 | 0.04 | 0.06 | 15.80 | 22.30 |
| 14 | 0.07 | 0.07 | 26.90 | 28.13 |
| 21 | 0.15 | 0.12 | 54.00 | 47.80 |
| 28 | 0.33 | 0.24 | 122.00 | 96.83 |
| 35 | 0.45 | 0.36 | 168.00 | 143.67 |
| 42 | 0.60 | 0.36 | 224.50 | 124.70 |

EXAMPLE 2

A plastic composition was prepared with 55% by weight of KRATON G copolymer, 20% by weight of n-butyryltri-n-hexyl citrate, and 25% by weight of polypropylene. The plastic composition was autoclavable and extrudable although some problems were encountered with the plies of film sticking together during autoclaving.

EXAMPLE 3

A plastic composition was prepared with 60% by weight of the KRATON G copolymer, 15% by weight of n-butyryltri-n-hexyl citrate, and 25% by weight of polypropylene. Although some difficulty in pelletizing the plastic composition was encountered, the plastic composition was successfully extruded into a film and autoclaved.

EXAMPLE 4

A plastic composition was prepared with 65% by weight of the KRATON G copolymer, 15% by weight of n-butyryltri-n-hexyl citrate, and 20% by weight of polypropylene. As in Example 3, the plastic composition was difficult to pelletize but extruded satisfactorily and was also autoclavable.

EXAMPLE 5

A plastic composition was prepared from 50% by weight of the KRATON G copolymer, 10% by weight of n-butyryltri-n-hexyl citrate ester, 20% by weight of polypropylene and 20% by weight of ethyl vinyl acetate. The plastic composition was mixed, pelletized and extruded into a film 0.013"±0.002 thick. The film was formed into a bag and autoclaved.

EXAMPLE 6

A plastic composition was prepared from 70% by weight of KRATON G and 30% of n-butyryltri-n-hexyl citrate ester. This composition was sticky and exhibited poor melt and tensile strength. The composition was discarded and no further work was performed on this particular composition.

EXAMPLE 7

A plastic composition was prepared from 55% by weight of KRATON G, 15% of n-butyryltri-n-hexyl citrate, 10% of ethyl vinyl acetate and 20% of polypropylene. The composition was pelletized, extruded, formed into a bag and autoclaved. It was observed that the autoclaving results could be improved by adding a mat finish or a wax.

EXAMPLE 8

A plastic composition was prepared from 45% of the KRATON G copolymer, 15% of n-butyryltri-n-hexyl citrate, 20% of the ethyl vinyl acetate and 20% of the polypropylene. The composition was pelletized, extruded, formed into a bag and autoclaved. The results were generally satisfactory although the film was somewhat sticky.

This description has been offered for illustrative purposes only and is not intended to limit the invention of this application, which is defined in the claims below.

What is claimed is:

1. A flexible, plastic container having a wall defined by a plurality of plastic layers, wherein one of said layers includes a composition comprising a polyolefin copolymer and a citrate ester, the quantity of said citrate ester being sufficient to suppress the hemolysis of red blood cells stored within said container.

2. A plastic container in accordance with claim 1 wherein said composition is the innermost layer of the wall.

3. A plastic container in accordance with claim 1 wherein said citrate ester provides a controlled leaching of said citrate ester into the blood in order to suppress the hemolysis of red blood cells.

4. A plastic container in accordance with claim 1 wherein said non-PVC copolymer is a polyolefin copolymer.

5. A plastic container in accordance with claim 1 wherein said non-PVC copolymer comprises:
a block copolymer, having thermoplastic rubber characteristics, consisting essentially of (1) a central block, comprising 50% to 85% by weight of the copolymer molecule, of a rubbery olefin polymer of generally equal proportions of ethylene and butylene units, and (2) terminal blocks of polystyrene.

6. A plastic container in accordance with claim 1 wherein said citrate ester is selected from the group consisting of acetyltri-n-hexyl citrate, n-butyryltri-n-hexyl citrate, acetyltri-n-hexyl/octyl/decyl) citrate, and acetyltri-n-(octyl/decyl) citrate.

7. A plastic container in accordance with claim 1 wherein said citrate ester is n-butyryltri-n-hexyl citrate.

8. A plastic container in accordance with claim 4 wherein said composition further comprises a selected quantity of polyolefin consisting essentially of propylene units.

9. A plastic container in accordance with claim 8 wherein said composition comprises from 20% to b 30% polyolefin consisting essentially of propylene units.

10. A plastic container in accordance with claim 8 wherein said composition comprises:
55% to 65% by weight of polyolefin copolymer;
15% to 25% by weight of citrate ester;
20% to 30% by weight of polyolefin consisting of essentially propylene units.

11. A plastic container in accordance with claim 6 wherein said citrate ester has heat stability characteristics, after heating at 150° C. for two hours, of a color not greater than 50 to 60 apha, and a mild odor at 25° C. and has an aconitate level of less than about 0.2% when the esterification mixture from which said citrate is produced tests 0.5% maximum acidity when calculated as citric acid.

12. A plastic container in accordance with claim 6 wherein said citrate ester has a heat stability characteristic, after hearing at 150° C. for two hours, of a neutralization number mg. KOH/g, of not greater than about 0.2.

13. A method of making a material suitable for fabricating a flexible, plastic container for storing red blood cells, said method comprising:
   providing a non-PVC plastic;
   mixing with said non-PVC plastic a citrate ester, the quantity of said citrate ester being sufficient to suppress hemolysis of red blood cells stored within said container; and
   forming said mixture into a flexible container for receiving red blood cells.

14. A method in accordance with claim 13 wherein said citrate ester provides a controlled leaching of said citrate ester into the blood in order to suppress the hemolysis of red blood cells.

15. A method in accordance with claim 13 wherein said non-PVC plastic is a polyolefin copolymer.

16. A method in accordance with claim 15 wherein the said polyolefin copolymer comprises:
   a block copolymer, having thermoplastic rubber characteristics, consisting essentially of (1) a central block, comprising 50% to 85% by weight of the copolymer molecule, of a rubbery olefin polymer of generally equal proportions of ethylene and butylene units, and (2) terminal blocks of polystyrene.

17. A method as described in claim 13 wherein said citrate ester is selected from the group consisting of acetyltri-n-hexyl citrate, n-butyryltri-n-hexyl citrate, acetyltri-n-hexyl/octyl/decyl) citrate, and acetyltri-n-(octyl/decyl) citrate.

18. A method in accordance with claim 13 wherein said citrate ester is n-butyryltri-n-hexyl citrate.

19. A method in accordance with claim 13 wherein the quantity of citrate ester is from 15% to 25% of dry weight.

20. A method in accordance with claim 15 wherein said method further comprises the step of mixing with said polyolefin copolymer a selected quantity of polyolefin consisting essentially of propylene units.

21. A method in accordance with claim 20 wherein said resultant material comprises:
   20% to 30% by weight of polyolefin consisting essentially of propylene units.

22. A method in accordance with claim 20 wherein said resultant material comprises:
   55% to 65% by weight of polyolefin copolymer;
   15% to 25% by weight of citrate ester;
   20% to 30% by weight of polyolefin consisting of essentially propylene units.

23. A method in accordance with claim 20 wherein said resultant material comprises:
   55% by weight of polyolefin copolymer;
   15% by weight of n-butyryltri-n-hexyl citrate;
   30% by weight of polyolefin consisting essentially of propylene units.

24. A method in accordance with claim 13, said method including the step of extruding the resultant material.

25. A method in accordance with claim 24 wherein said extruding step comprises extruding said resultant material into a film of selected thickness.

26. A method as described in claim 24 wherein said resultant material is co-extruded with a different material.

27. A method in accordance with claim 25, said method further including the step of forming said film into a selected container shape.

28. A method of making a material suitable for fabricating a flexible, plastic container for storing red blood cells, said method comprising:
   providing a polyolefin co-polymer wherein said polyolefin co-polymer comprises:
      a block co-polymer, having thermoplastic rubber characteristics, consisting essentially of (1) a central block, comprising 50% to 85% by weight of the co-polymer molecule, of a rubbery olefin polymer of generally equal proportions of ethylene and butylene units, and (2) terminal blocks of polystyrene;
   mixing a citrate ester with said polyolefin copolymer, the quantity of said citrate ester being sufficient, when said mixture is formed into a flexible red blood receiving container, to suppress hemolysis of red blood cells stored within said container.

* * * * *